United States Patent
Fleming et al.

(10) Patent No.: US 6,532,820 B1
(45) Date of Patent: Mar. 18, 2003

(54) COMBINED ULTRASONIC TECHNIQUES FOR EVALUATIONS (CUTE)

(76) Inventors: Marvin F. Fleming, 1480 Montclaire Pl., Los Altos, CA (US) 94024; Jack P. Clark, 107 Cappy Ct., San Jose, CA (US) 95111; Robert M. Clark, 3599 S. Bascom Ave., #49, Campbell, CA (US) 95008

( * ) Notice: Subject to any disclaimer, the term of this patent is extended or adjusted under 35 U.S.C. 154(b) by 0 days.

(21) Appl. No.: 09/890,616
(22) PCT Filed: Jan. 5, 2000
(86) PCT No.: PCT/US00/00220
§ 371 (c)(1), (2), (4) Date: Aug. 2, 2001
(87) PCT Pub. No.: WO00/40960
PCT Pub. Date: Jul. 13, 2000

(51) Int. Cl.[7] .............................................. G01N 29/00
(52) U.S. Cl. .......................................... 73/627; 73/620
(58) Field of Search ........................ 73/596, 602, 618, 73/619, 620, 625, 627, 628

(56) References Cited

U.S. PATENT DOCUMENTS

| | | | |
|---|---|---|---|
| 4,327,738 A | 5/1982 | Green et al. | 128/660 |
| 4,836,026 A | 6/1989 | P'an et al. | 73/620 |
| 4,865,040 A | 9/1989 | Ogasawara | 128/661.04 |
| 5,282,471 A | 2/1994 | Sato | 128/660.07 |
| 5,750,895 A * | 5/1998 | Chern et al. | 73/614 |
| 5,797,844 A | 8/1998 | Yoshioka et al. | 600/442 |

OTHER PUBLICATIONS

J.A. Jones Applied Research Company, Charlotte, North Carolina, Automatic Sizing of Intergranular Stress Corrosion Cracking With IntraSpect/98, EPRI NP–5409, Project 1570–2, Topical Report, Sep. 1997.

* cited by examiner

Primary Examiner—Richard A. Moller
(74) Attorney, Agent, or Firm—Allston L. Jones (57) ABSTRACT

An ultrasonic image process and system for accurately evaluating the quality of a weld using ultrasonic responses and operator entered data to enhance the quality of weld inspection. Ultrasonic responses useful in accurately indicating the actual location of the weldment, detecting the actual component thickness and the location and characteristic of any other relevant ultrasonic reflectors located in or near the weld heat effected zone are input to a composite image of a weldment for the purpose of enhancing the quality and the ease of detecting, evaluating and sizing of weld defects. Through the superposition of ultrasonic image data from additional complimentary sensors and operator inputs based on prior known data, useful images can be formed to improve the decision making in weldment inspection and evaluation.

14 Claims, 12 Drawing Sheets

Images From Channel 2

7 Image of Outside Surface (Profile)

Figure 8b

COMBINED ULTRASONIC TECHNIQUES FOR EVALUATIONS (CUTE)

FIELD OF THE INVENTION

The present invention relates to ultrasonic imaging of a workpiece to locate and analyze features in a workpiece for evaluating the quality of the workpiece. For example in analyzing a weldment, the analysis is enhanced by combining certain imaging features to assist in identifying the location of the basemetal to weld interface, the weld thickness and location of toe, the basemetal thickness, the location of the external surface geometry, and to do this from both sides of the weld; ostensibly to locate defects of any size and orientation. More specifically, to do so using sonic technology.

PRIOR ART

Commercial ultrasonic imaging equipment, such as the UTV-400 by Sierra Matrix, the IntraSpect 98 and others conventionally uses A-, B-, B'- and C-scans for evaluation of work pieces. Some of the prior art related to this field are:

U.S. Pat. No. 4,836,026: ULTRASONIC IMAGING SYSTEM;

U.S. Pat. No. 5,797,844: METHOD AND APPARATUS FOR ULTRASONIC IMAGING AND ULTRASONIC IMAGE PROCESSING;

U.S. Pat. No. 4,865,040: ULTRASONIC IMAGE RECORDING METHOD AND SYSTEM;

U.S. Pat. No. 4,327,738: ENDOSCOPIC METHOD & APPARATUS INCLUDING ULTRASONIC B-SCAN IMAGING; and U.S. Pat. No. 5,282,471: ULTRASONIC IMAGING SYSTEM CAPABLE OF DISPLAYING 3-DIMENSIONAL ANGIOGRAM IN REAL TIME MODE.

SUMMARY OF THE INVENTION

The present invention is an ultrasonic imaging method and system that speeds-up and accurately evaluates the quality of a workpiece using ultrasonic responses and operator entered data to enhance the quality of workpiece evaluation. The present invention includes a multichannel ultrasonic imaging system to obtain and display a combination of processed ultrasonic responses from reflectors within the workpiece to locate, classify and isolate the various ultrasonic responses. This is accomplished by the technique of the present invention for creating a combined image from the ultrasonic responses of the multiplicity of transducers to aid in the accuracy, speed and confidence in the results.

The present invention uses the scanning position of two or more ultrasonic transducers and the ultrasonic response received from reflectors within the workpiece (or workspace, as the case may for air or water) to form a superimposed B-scan using specially processed data from the ultrasonic transducers and from auxiliary measurements of the workpiece.

BRIEF DESCRIPTION OF THE FIGURES

FIG. 5b is the image for the first channel data obtained from the workpiece shown in FIG. 5a.

FIG. 6b is the image for the second channel data obtained from the workpiece shown in FIG. 6a.

FIG. 7b is the image for the third channel data obtained from the workpiece shown in FIG. 7a.

FIG. 8b is the image for the fourth channel data obtained from the workpiece shown in FIG. 8a.

DESCRIPTION OF THE PRESENT INVENTION

The system and techniques of the present invention are used to inspect various materials for internal flaws, failures and anomalies that may occur over time. Many materials that are the focus of ultrasonic testing are various materials that are used in construction of buildings, bridges and other structures. Weldments that join two elements are often the focus of such inspections. In the discussion of the present invention that follows, the examples given to illustrate the present invention are the detection of flaws or figures in weldments, however the present invention is by no means limited to the inspection of weldments. The techniques and equipment disclosed herein are equally applicable to the detection of various flaws, failures and anomalies of various types in various materials, including air and water.

For example, in weldment evaluation, ultrasonic responses are useful in accurately indicating the actual location of the weldment in the base metal, detecting the actual component thickness and the location and characteristic of any other relevant ultrasonic responses located in or near the weld heat effected zone. In the present invention, these responses are utilized to form a composite image of a weldment to enhance the quality and the ease of detecting, evaluating and sizing of weld defects as will be seen from the following discussion. Through the superposition of ultrasonic image data from additional complimentary sensors and operator inputs based on prior known data, enhanced and useful images are formed that improve the decision making in workpiece inspection and evaluation.

Another example of the application of the present invention is the detection and discrimination of crack like defects and impurity inclusion in a rectangular workpiece where the ultrasonic image from a spherical inclusions can be confused with those from planar cracks wherever the sound beam arrives from along the normal to the crack surface. By using the present invention to display a composite B-scan using two or more transducers located to position their sound beams along two orthogonal axis produces superimposed B-scan image that improves the classification of inclusion and crack type defects. Unlike the previous example, processing of both ultrasonic channels can be identical in this example. data channels 1 and 2, associated with transducers 1 and 2 in FIG. 1 is a specific example where the ultrasonic channels are the same but use different angles for propagating the corresponding ultrasonic beam to the workpiece, and for drawing the resulting image from each.

Still another example of am application for the present invention is the use of two channels of different frequency transducers to distinguish the location of the transition zone between two materials. In such an application, the frequency of the transducers are selected such that one transducer frequency will penetrate both material types, while the second transducer frequency is selected to be reflected from one of the materials. In this application of the present invention, both transducer beams are oriented in the same direction with the material response to the two transducer frequencies enables measurement of the overall thickness of the two materials and the thickness to the transition zone from the transparent material side. A specific example of using two channels, both using ultrasonic transducers having beams oriented perpendicular to surface 7 as shown for channel 1 in FIG. 1, and using the same B-scan imaging techniques for both channels. The significant difference here being that one channel uses a lower frequency where both materials are transparent and the other channel uses a higher frequency where the distant layer is nearly, or completely opaque. One practical application for this two channel version of the present invention is in the examination of individual thickness and the overall thickness of stainless steel and carbon steel. For example one transducer could use 2 mHz for channel 1 to make the overall thickness measurement, and the other transducer could use 15 mHz for channel 2 to more easily observe the stainless steel thickness.

Note, that the text and figures as discussed below is merely one example of the application of the present invention. In the broadest form, the present invention can be performed with only two channels of data, or with more than two channels of data. Initially, a two or more, channel system for weld inspection is discussed using FIGS. 1 and 2a to describe the method and apparatus of the present invention. Later, in an extension of the example of FIGS. 1 and 2a, another method of superimposing images is described. The number and combination of channels needed is dependant on the specific application and problem being addressed. If the surface profile 7 is unknown, or varying, then using transducers 2 and 4 as shown in FIG. 1 is useful for locating and detecting anomalies in workpiece 8. Also, if the anomalies occur near weldment 13, then transducer 2 can be configured to use an ultrasonic frequency that renders both the base material and the weldment practically transparent while configuring transducer 3 to use a higher frequency at which the weldment portion of the workpiece provides a greater response than the base metal in the weldment. For example, transducer 2 could use 2 mHz to make both the base metal and the weldment transparent and transducer 3 could use 15 mHz to increase the response from the weldment. In still other cases, where the abnormalities occur along the opposite side of the workpiece, the use of transducers 1 and 2 would be usefull. It follows then that the number and the specific configuration of each transducer and associated channel depends on the nature of the problem to be evaluated. In some applications the use of three transducers, or even all four, would prove useful.

Figure 1:
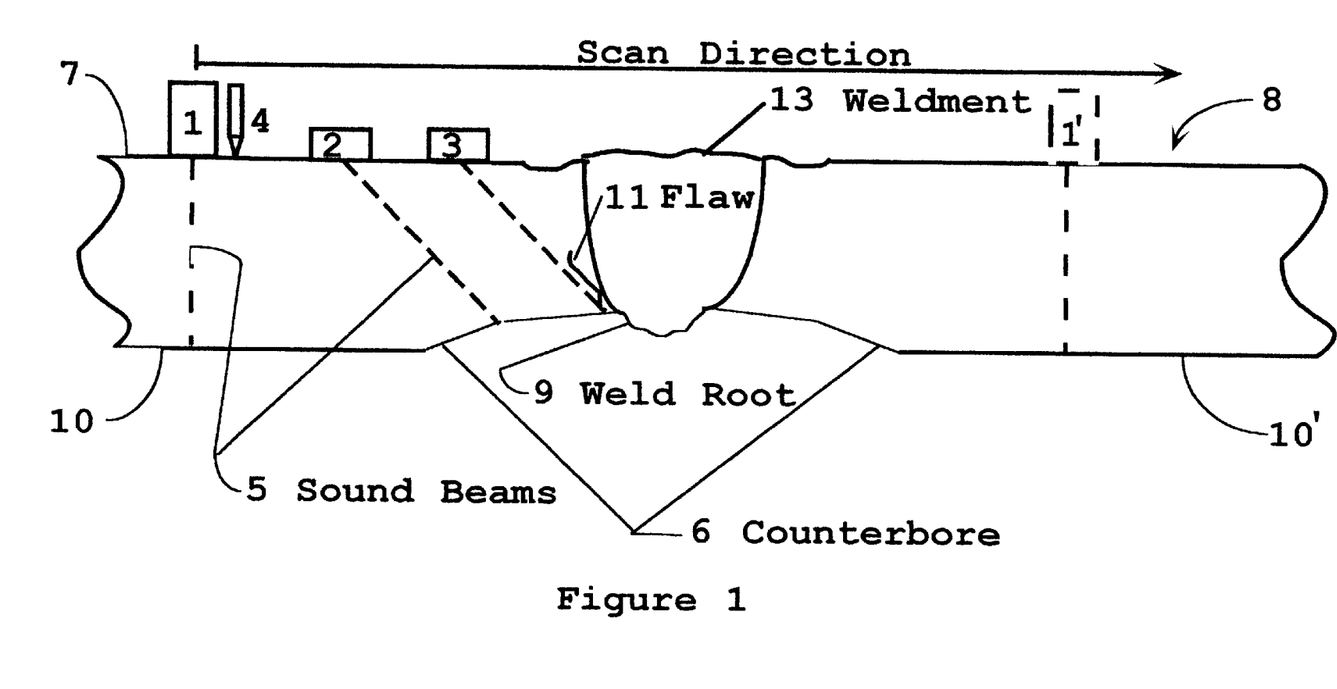
FIG. 1 is a cross-sectional view of a welded workpiece that is being examined with four channels of data in accordance with the present invention.
Figure 2:
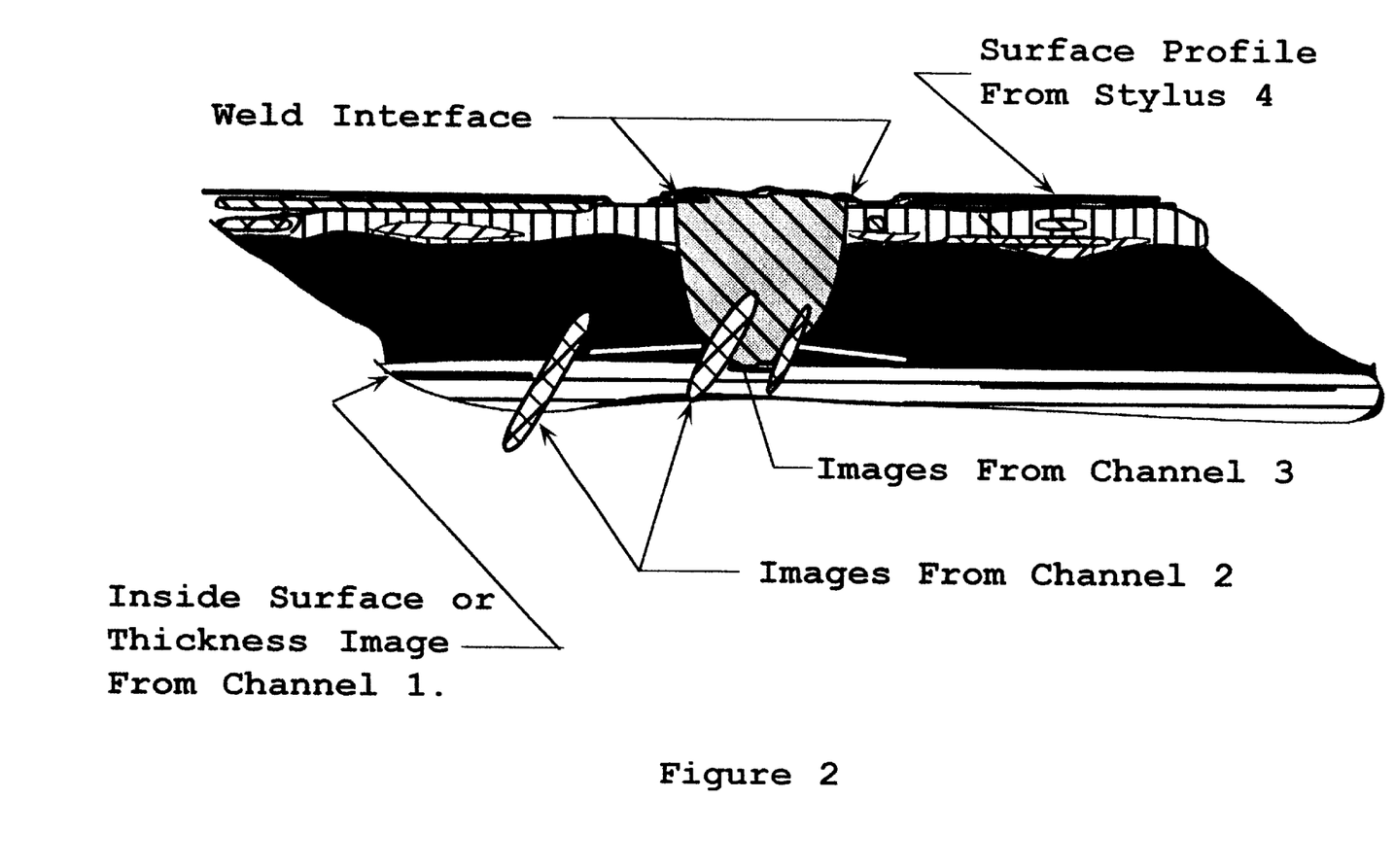
FIG. 2 illustrates the superpositioning of images produced by four channels of data obtained from the workpiece shown in Figure.

FIG. 1 is a crosssectional view of a welded workpiece 8 with weldment 13 joining two pieces 10 and 10' to create the overall workpiece 8. Typical features of such a weldment are counterbore 7 and weld root 9 on the lower side of the overall weldment 13. Also, to illustrate the present invention, a flaw 11 has been included in close proximity to the lower left side of weldment 13. Additionally, for purposes of discussion of the present invention, a scan direction from left to right for the transducers relative to the workpiece has been shown, however one familiar with ultrasonic testing will understand that the direction of scan is not important since the same results will be obtained for either scan direction.

In FIG. 1 four transducers are shown for use in the present invention for examining a workpiece, more particularly weldment 13 in the example used here. A first channel of data is provided by transducer 1 to measure the actual thickness of the workpiece. A second channel of data is obtained with transducer 2 which is configured to detect features related to quality. A third channel of data is obtained with transducer 3 which is configured to detect the weldment in the workpiece. A fourth channel of data is provided by sensor 4 (e.g., a stylus and related electronics) to measure the surface profile of workpiece 8 that is being scanned.

More specifically, the ultrasonic imaging system as shown in FIG. 1 uses multiple ultrasonic transducers to acquire ultrasonic data from the workpiece. Three ultrasonic transducers are used in the example; each chosen to gather information useful for workpiece evaluation. Transducer 1 provides an ultrasonic beam normal to the surface of the workpiece to measure material thickness on channel 1; transducer 2 generates a second ultrasonic beam that is directed at an angle relative to the surface of the workpiece, such as 45 degrees, for detecting cracked corners of the weldment; and transducer 3 provides another ultrasonic beam directed at an angle to the surface of the workpiece with an orientation similar to the second beam at perhaps a different (higher) frequency to easily develop responses from the grain structure in the weldment. The selection of transducer frequency, the direction of the beam angles, the type of processing preferred for each channel is at the discretion of the ultrasonic experts using the present invention to optimize their selection of transducers, other components required, schedules and cost.

FIG. 2 illustrates one embodiment of the present invention that consists of a composite B-scan image generated by the superpositioning of the different individual B-scan images from the various transducers shown in FIG. 1 relative to each other to highlight the features of significance in the evaluation of workpiece 8. The superpositioned images are various types of B-scan images that are produced from the data generated by the four transducers shown in FIG. 1. The first channel B-scan from transducer 1 reports the actual thickness of base metal and weldment as indicated in FIG. 2. Further, the second channel B-scan from transducer 2 locates inclusions, cracks, weld preparations, weld root and spurious ultrasonic reflectors also indicated in FIG. 2. Note, the image from the second channel is used by prior art systems without the other images being superimposed. Then the image from the third channel B-scan to detects and shows the dendritic structure in the weldment and provides important evaluation information as to the location of the heat-effected-zone around weldment 13 also shown in FIG. 2. The third channel B-scan, like the first channel B-scan, in this example uses threshold levels to detect the location of ultrasonic reflectors resulting in the production of a series of measurements that appear as broken lines in the individual or in the superimposed B-scan (see FIG. 2). The fourth channel in the present example includes information derived from the output of a linear potentiometer connected to a stylus that follows the outside surface of the workpiece during the scan. The output from that linear potentiometer is then used to reference a starting point for the individual ultrasonic B-scans; and, having the same outside surface reference provides the basis for scaling individual B-scans to a common display scale. Having the outside surface reference also provides a basis for constructing the individual B-scans relative to the actual outside surface orientation.

To create the superposition of the various images as describe above the various transducers can be scanned across the surface of workpiece 8 in any order (the order shown in FIG. 1 is for illustration only) and with any spacing between them. To be able to provide the superpositioned image of the present invention, however, the specific selected order and spacing of the transducers relative to each other must be known and remain unchanged during the scan. Knowing that order and spacing of the transducers, the images created by three of the transducers can then be time shifted the appropriate amount to permit the superpositioning of one image on the others such that the features detected and contributed by each individual image are aligned with each other. This alignment of the of the various images thus produces a single image that relates directly with the position of those features in the physical workpiece 8. Additionally, the images shown here in the various figures are generated with the use of a color algorithm wherein each color represents a different signal amplitude of the corresponding B-scan.

Figure 3:
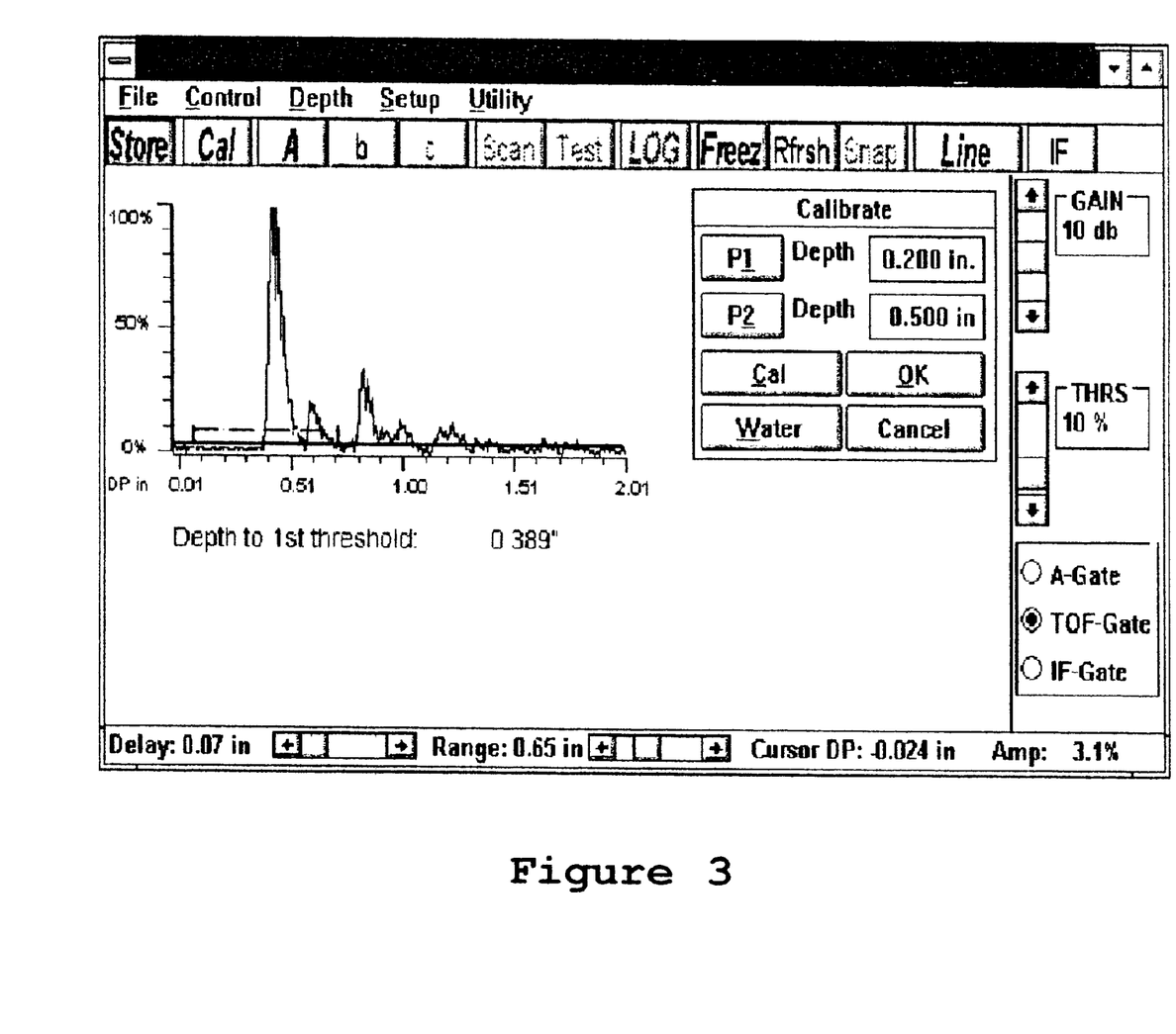
FIG. 3 is an A-scan plot of the data on channel 2 of FIG. 1 showing the first threshold detection reading from the workpiece.

More specifically, FIG. 2 shows a composite B-scan having superimposed images of the B-scan images from transducers 1, 2 and 3. The B-scan from transducer 2 used in this example as one where the amplitude of the ultrasonic signal is represented using a color scale (this includes the use of a gray scale). The B-scan from transducer 1 uses a contrasting color (e.g., white) as in FIG. 2 for superimposing the two B-scans from transducers 1 and 2. The B-scan from transducer 1 is using an A-scan threshold technique in this example as illustrated in FIG. 3. In this case it simplifies the construction of a superimposed B-scan because the information required from transducer 1 is material thickness for the base material and the weld material transducer 3 in the example shown in FIG. 1 has the function of identifying the dendritic structure in the weld which will locate the heat effected zone in the basemetal adjacent to the dendritic structure in the weld. The B-scan for transducer 3 will use the same A-scan threshold technique and contrasting line color algorithm as described for transducer 1.

FIG. 3 is an A-scan plot of the data generated by transducer 2 of FIG. 1 showing a first threshold detection reading from workpiece 8. Making a B-scan from a series of appropriately related A-scans is well known in the art and is described in the Prior Art references noted above.

Figure 4:
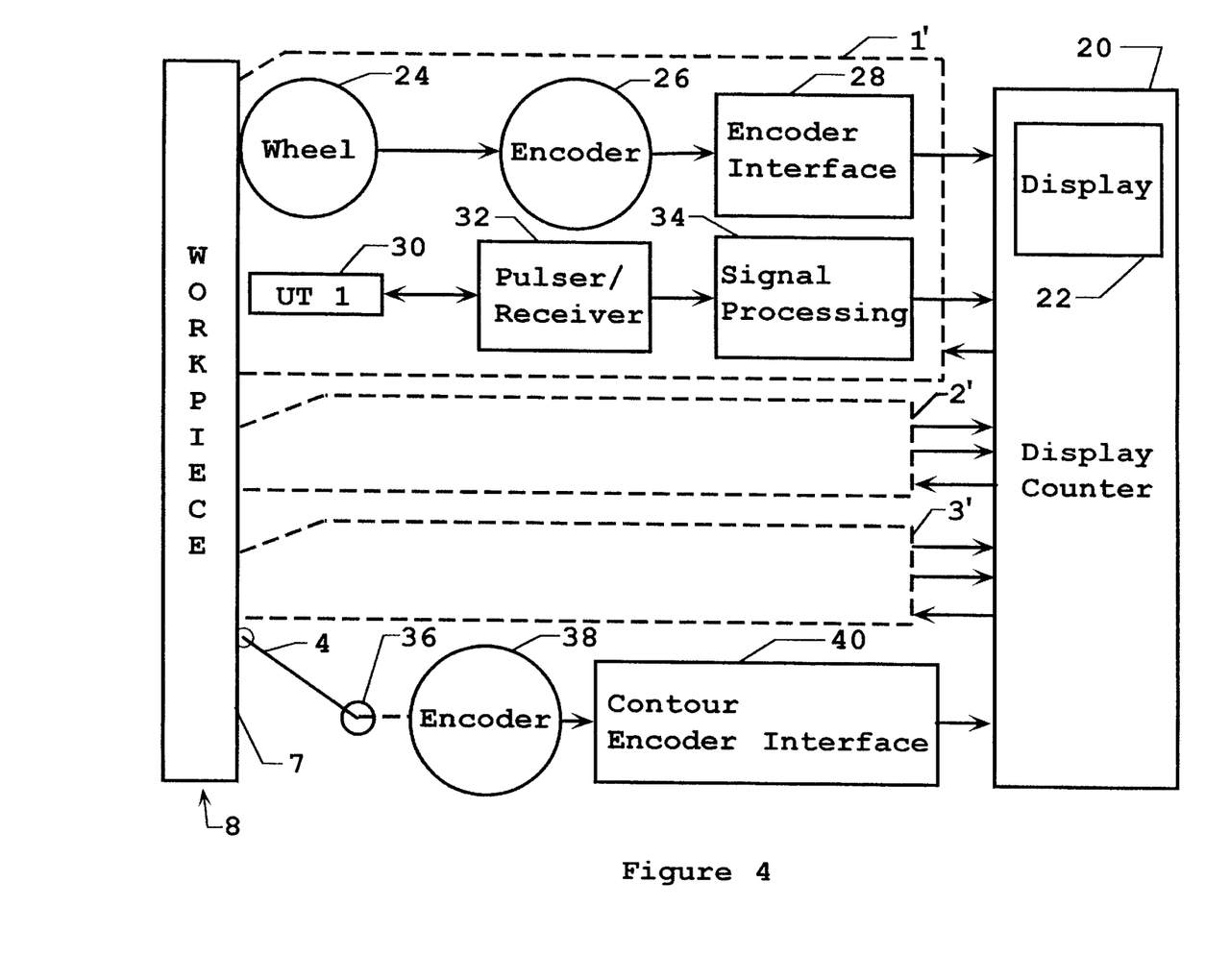
FIG. 4 is a block diagram of the ultrasonic testing unit of the present invention.

FIG. 4 provides a block diagram of the scanning system of the present invention. Along the left edge of FIG. 4 is workpiece 8 to illustrate the interaction of the scanning system of the present invention with workpiece 8. Progressing to the right, the four transducers and corresponding data channel are shown. There three B-scan channels are the same so the detail, of the first is the only one that shows the internal components in detail. To relate the various channel electronics shown in FIG. 4 to the transducers shown in FIG. 1, the channel electronics that correspond to transducers 1, 2 and 3 have been labeled in FIG. 4 as 1', 2' and 3'. The fourth channel includes stylus 4 in contact with surface 7 of workpiece 8 to provide a profile of surface 7 as the scan progresses across workpiece 8. The electronics of each channel additionally interfaces with computer 20 having a display 22 to control the operation of the scan and to process the data signals received from each of the data channels as described below. Computer 20 is instructed by the user as to how the data is to be presented and which transducer responses are to be presented superpositioned with respect to each other.

Each of ultrasonic channel electronics 1', 2' and 3' includes two data paths, one path to determine the distance and direction traversed in the scan, and a second path to provide the ultrasonic excitation and to listen for a reflection of that excitation to and from workpiece 8. The distance/direction path includes a wheel 24 in contact with surface 7 of workpiece 8 to rotate as a scan proceeds, with wheel 24 driving an encoder 26 which determines the extent and direction of travel during a scan. The information from encoder 26 is then provided to encoder interface 28 which formats the signal for use by, and hands off that signal to, computer 20 for generation of the scan data as requested by the user. The ultrasonic path includes an ultrasonic transducer 30 that both radiates an ultrasonic signal of a selected frequency, duration, intensity and angle, toward workpiece 8, and detects ultrasonic reflections from workpiece 8. Ultrasonic transducer 30 is directly connected to pulser/encoder 32 which controls the pulse frequency, duration and intensity of the ultrasonic signal applied to workpiece 8 by transducer 30 (the angle is determined by the placement and type of transducer 30), as well as receiving signals from transducer 30 that correspond to reflections detected by transducer 30. The from pulser/receiver 32, the received signal is applied to signal processing 34 and then to computer 20.

The fourth channel in addition to stylus 4 includes a spring 36 to keep stylus 4 in contact with surface 7 of workpiece 8 throughout the scan. Additionally, stylus 4 is mechanically coupled to encoder 38 that generates a signal the corresponds to the actual position of stylus 4. For example, encoder 38 could be a potentiometer where the contact finger is mechanically coupled to stylus 4 to vary the resistance in response to changes in surface 7. Encoder 38 in turn is connected to a contour encoder interface 40 that then provides a signal that corresponds to the contour of surface 7 to computer 20.

Each of the implementations of the four channel electronics is substantially the same as in prior art instruments, however the inclusion of all four channels and their interfacing with the computer and the composite image that results is one of the features of the present invention.

Computer 20 is designed to display ultrasonic B-scans from the ultrasonic channels 1', 2' and 3'. Additionally, computer 20 generates the user selected output representations by superpositioning the necessary scan data to meet that request. To generate the desired presentation of the data in accordance with the present invention utilizes the data provided by any two or more of the four channels.

In the four channel system of FIG. 4 for use in the examination of workpiece 8 in FIG. 1 using the corresponding channels, B-scans used are of tow commonly used types: (1) a threshold type where the point in time that the A-scan signal exceeds a threshold is processed into a transition point in the B-scan (this results in a series of points that generally form a line being constructed on the B-scan) and is commonly used to make B-scans showing thickness or location of weldments, and (2) B-scans where the amplitude of the A-scan is mapped to a color value, frequently called a palette. In the discussions here it is convenient to use threshold B-scans for channels 1 and 4 that correspond to transducers 1 and 4, amplitude B-scans for channel 2 that corresponds to transducer 2, and either threshold or amplitude B-scans for channel 3 that corresponds to transducer 4. It is the combination of B-scan types that makes it practical to display the essential information from the four channels in a single composite image. The ultrasonic data from transducer 1 as used in the example of FIG. 1 is called an "amplitude type of B-scan" where display 22 and computer 20 makes an amplitude type B-scan from A-scan data shown in FIG. 3. Typically the A-scan in FIG. 2 uses a color bar to represent amplitude as a function of time (or depth) as shown in FIG. 3. Thus the amplitude vs time of FIG. 3 is converted to a line that changes color as a function of depth. That color line is shown on display 22 in proportion to the orientation of the beam in workpiece 8. As the transducer is scan across workpiece 8, the corresponding encoder 26 provides a changing signal that is used to draw the new line at a corresponding position on the display. If workpiece 8 is not flat, the contour interface information provided by encoder 38 is used by computer 20 to adjust the starting point of the line drawn on display 22. It should be clear that for instruments used in the field display 22 may not be physically large enough to display the entire image that is computed. Commercial systems accommodate this limitation of display 22 by various means (e.g., allowing the user to shift the image from side to side to view the entire image, and to store each image to storage device for later printout and inspection).

The use of certain variations in B-scan types is done in the present invention as a means for enhancing the composite image; such variations include the use of more than a single pixel in the horizontal or vertical direction of the display to denote the threshold in the B-scan (sometimes it is advantageous to use pixels or contrasting colors to make an event more observable). Another type of B-scan recognized as advantageous in the present invention is the B"-scan which is sometimes used to denote that the B-scan is taken from another surface path angled, usually at 90°, relative to the direction of the reference path for constructing a B-scan. These conventions are simply noted here as a reference to common convention and is not intended to limit the present invention to these types of scans.

The use of superimposed images includes the ability to also turn off the superimposed modes described above in a manner that allows individual images to be examined. Another feature provides the ability to sequence the individual images at a slow rate to allow the information from individual images to be observed separately, continuously superimposed or at operator controlled rates.

Figure 5A:
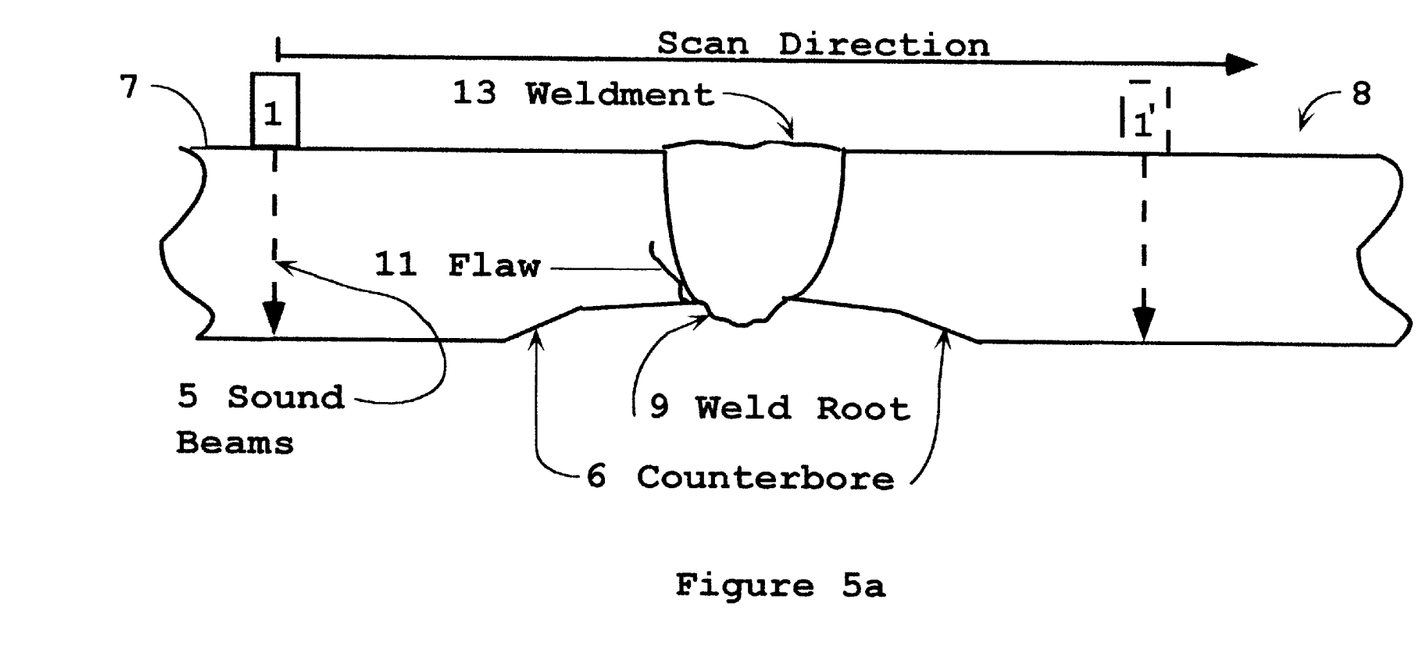
FIG. 5a is a cross-sectional view of the same welded workpiece as in FIG. 1 with only the first channel transducer of the system of the present invention shown.
Figure 5B:
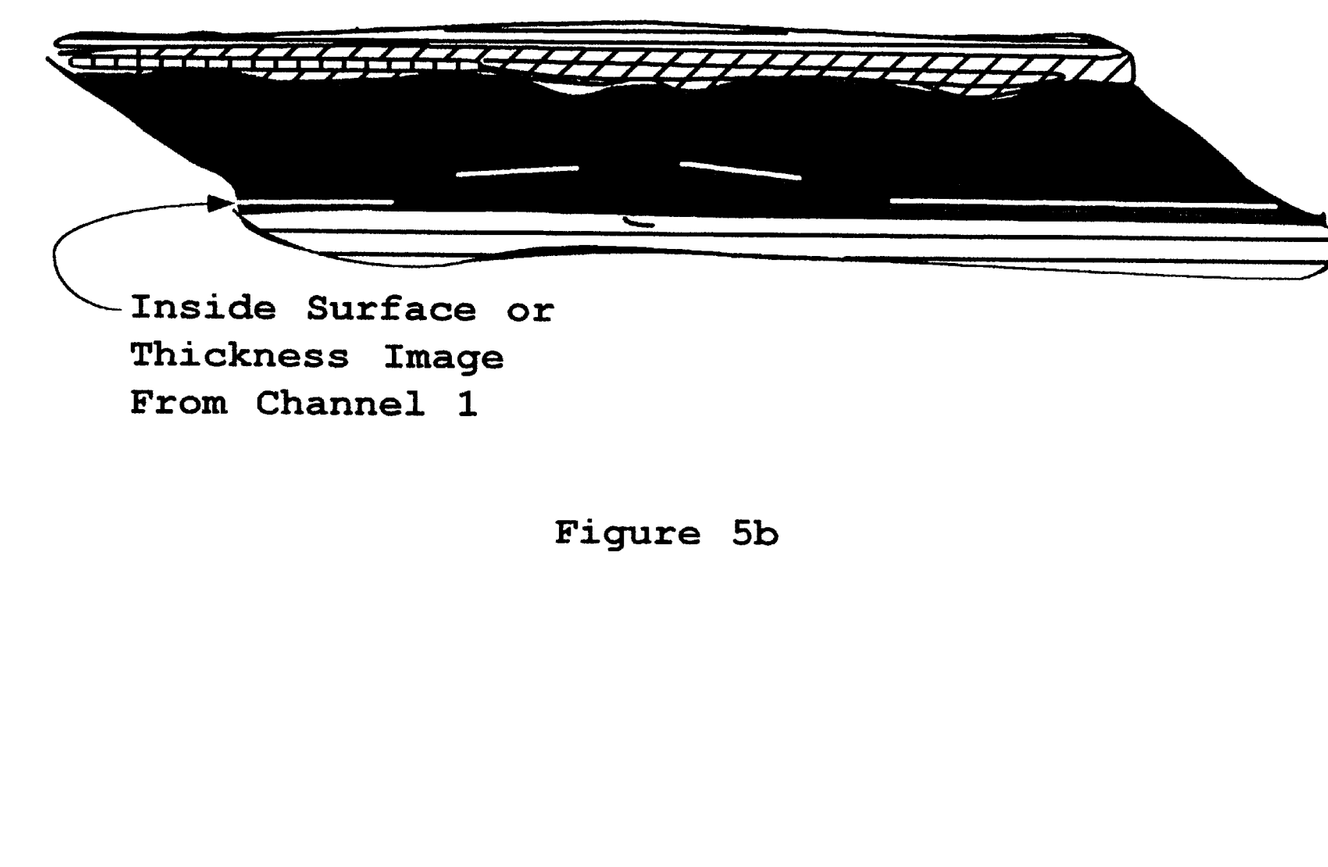
Figure 6A:
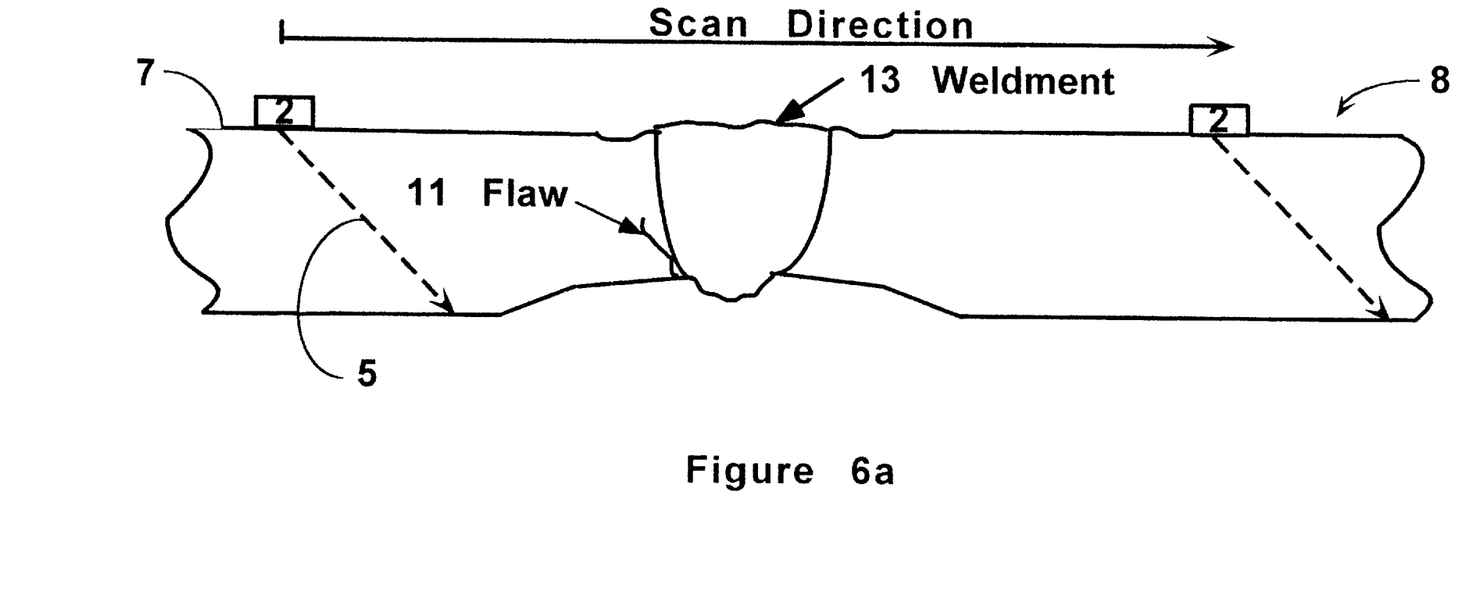
FIG. 6a is a cross-sectional view of the same welded workpiece as in FIG. 1 with only the second channel transducer of the system of the present invention shown.
Figure 6B:
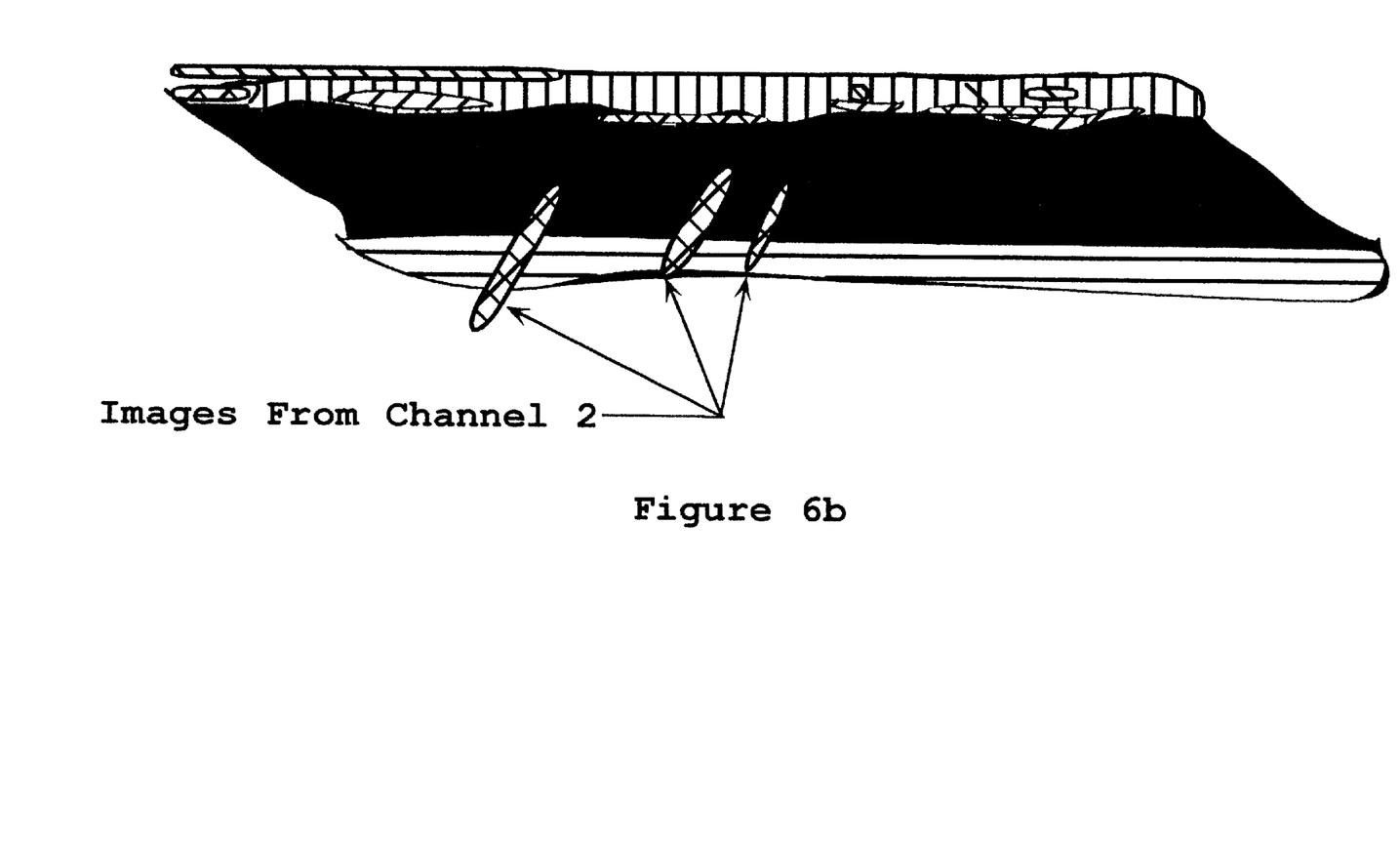
Figure 7A:
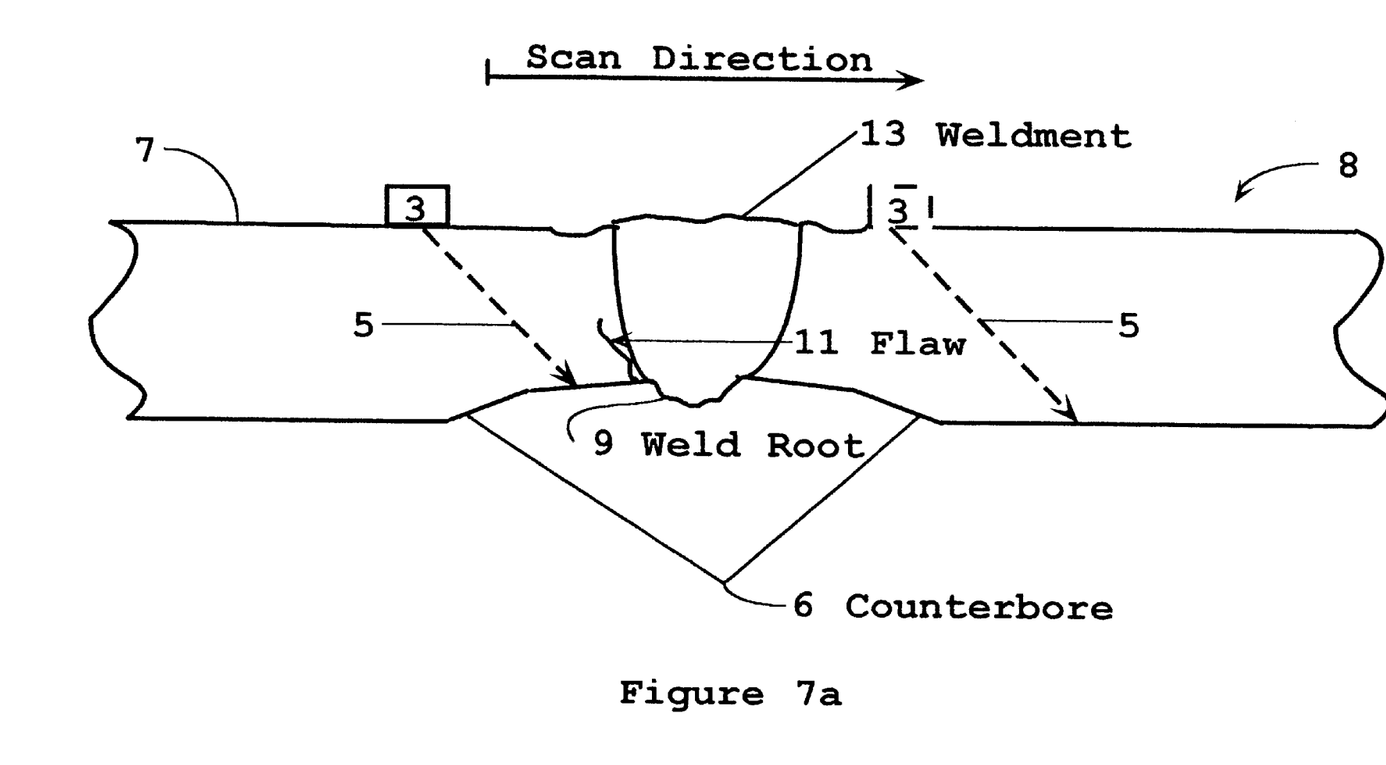
FIG. 7a is a cross-sectional view of the same welded workpiece as in FIG. 1 with only the third channel transducer of the system of the present invention shown.
Figure 7B:
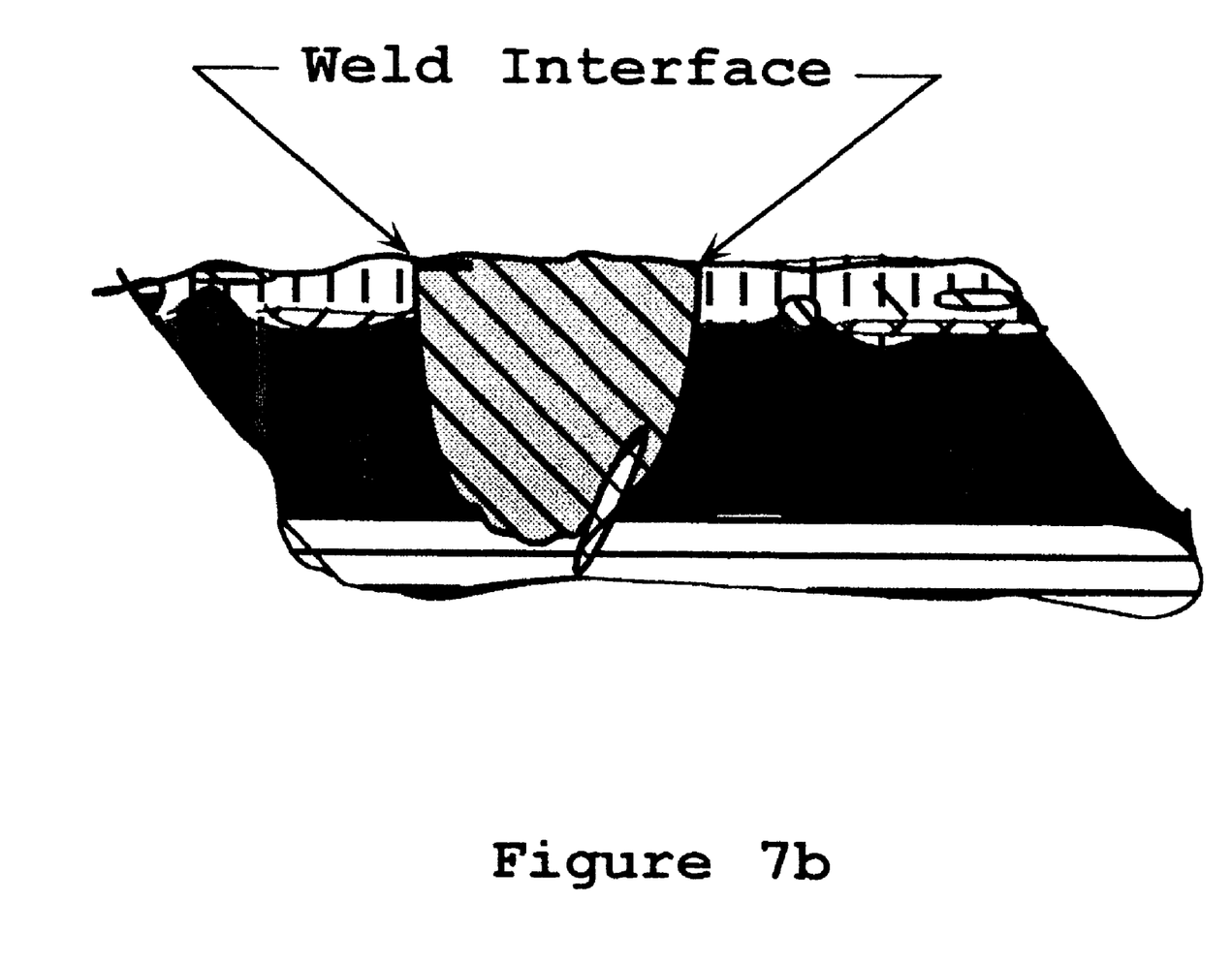
Figure 8A:
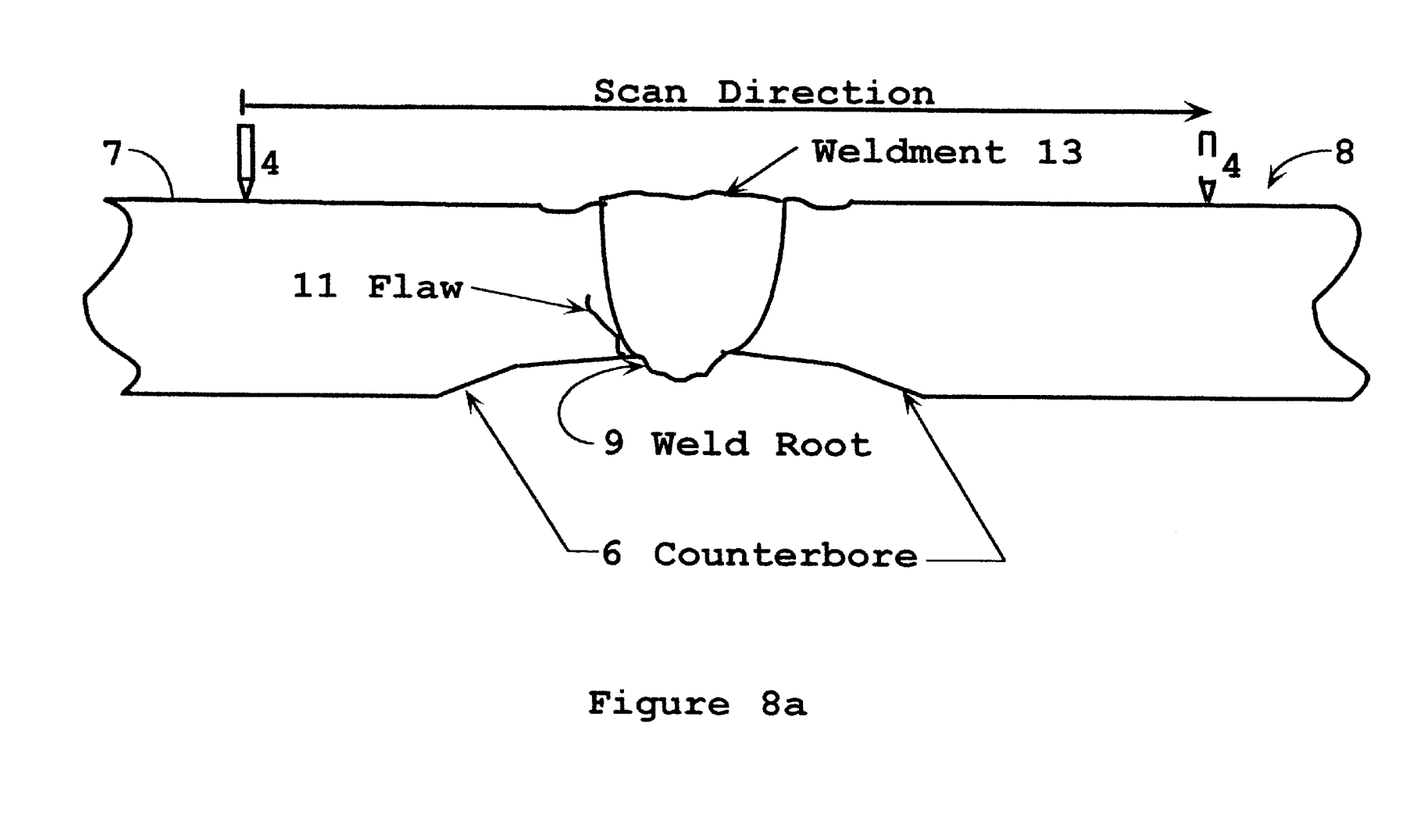
FIG. 8a is a cross-sectional view of the same welded workpiece as in FIG. 1 with only the fourth channel transducer of the system of the present invention shown.
Figure 8B:
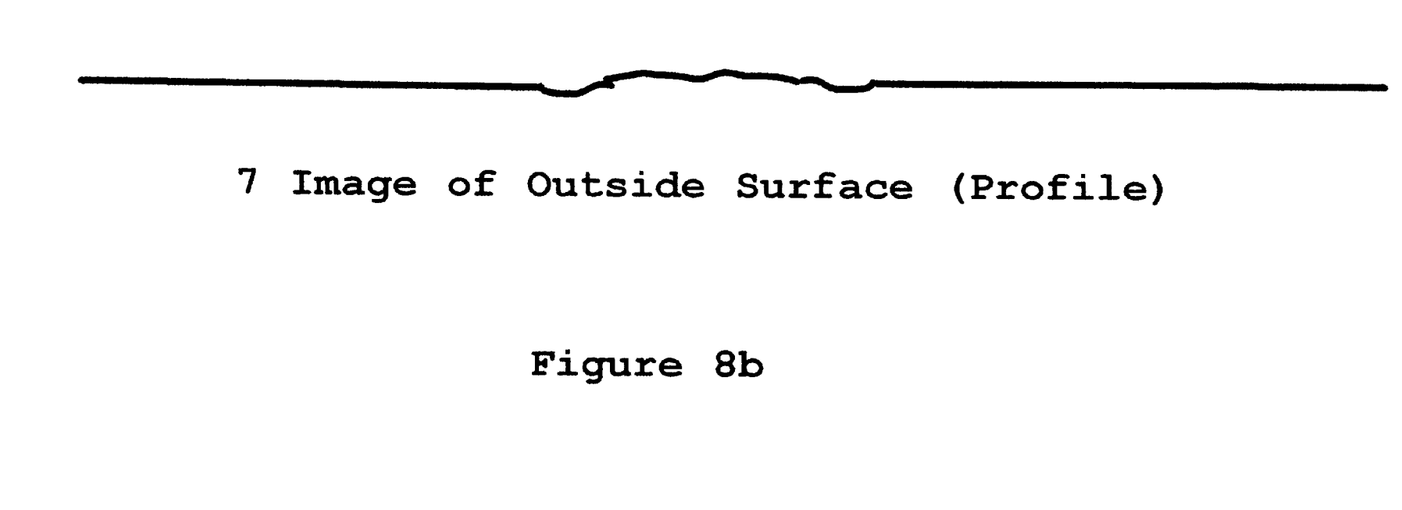

FIGS. 5a through 8b illustrate the individual images that have been superpositioned to create the composite image shown in FIG. 2. More specifically, FIG. 5a presents a cross-sectional view of the same welded workpiece 8 as in FIG. 1 with only the first channel transducer 1 shown. FIG. 5b is the image for the first channel data obtained from only transducer 1 of workpiece 8 as shown in FIG. 5a. Similarly, FIG. 6a is a cross-sectional view of the same welded workpiece 8 as in FIG. 1 with only the second channel transducer 2 shown, and FIG. 6b provides the image for the second channel data obtained from transducer 2 of workpiece 8 as shown in FIG. 6a. Continuing, FIG. 7a is a cross-sectional view of the same welded workpiece 8 as in FIG. 1 with only the third channel transducer 3 shown, and FIG. 7b provides the image for the third channel data obtained from transducer 3 of workpiece 8 as shown in FIG. 7a. Additionally, FIG. 8a is a cross-sectional view of the same welded workpiece 8 as in FIG. 1 with only the fourth channel transducer 4 shown, and FIG. 8b shows the image (i.e., workpiece surface profile) for the fourth channel data obtained from transducer 4 of workpiece 8 as shown in FIG. 8a.

What is claimed is:

1. A method for producing a superpositioned ultrasonic B-scan image of a workpiece having a top and bottom surface to locate flaws, failures and anomalies of various types in a variety of materials, and to map external surface geometry with a multichannel ultrasonic imaging system, said method comprising the steps of:
   a. directing a first sonic beam of a first frequency from a first channel of said multichannel ultrasonic imaging system toward a first surface of said workpiece at a first angle with respect to said first surface as said workpiece is scanned;
   b. utilizing a second channel of said multichannel imaging system to exercise said first surface of said workpiece as said workpiece is scanned;
   c. detecting reflections of said first sonic beam from said workpiece over time;
   d. developing a B-scan image from said detected reflections of said first sonic beam from step c.;
   e. detecting data from said second channel;
   f. developing an image from said detected data from said second channel; and
   g. superpositioning said B-scan image of step d. with said image of step f. to create a composite of said images from which to determine the existence and location of various detected features of said workpiece.

2. The method as in claim 1 wherein:
   step b. consists of the step of:
     h. directing a second sonic beam of a second frequency from said second channel of said multichannel ultrasonic imaging system toward said first surface of said workpiece at a second angle with respect to said first surface as said workpiece is scanned;
   step e. consists of the step of:
     i. detecting reflections of said second sonic beam from said workpiece over time;
   step f. consists of the step of:
     j. independently developing a B-scan image from said detected reflections of said second sonic beam from step i.; and
   step g. consists of the step of:
     k. superpositioning said B-scan image of step d. with said B-scan image of step j. to create a composite of said B-scan images from which to determine the existence and location of various detected features of said workpiece.

3. The method as in claim 1 wherein:
   step b. consists of the step of:
     h. positioning a stylus in contact with said first surface of said workpiece to follow a profile of said first surface as said workpiece is scanned;
   step e. consists of the step of:
     i. electronically monitoring positions of said stylus of step h. to develop an signal corresponding to said profile of said first surface as said workpiece is scanned;
   step f. consists of the step of:
     j. independently developing an image of said profile of said fist surface from said signal from step i.; and step g. consists of the step of:
  k. superpositioning said B-scan image of step d. with said profile image of step j. to create a composite image from which to determine the existence and location of various detected features of said workpiece.

4. The method as in claim 1 wherein:
a relative spacing between a first point on said first surface where step a. acts and a second point on said first surface where step b. acts is known; and
step g. consists of the steps of:
  h. offsetting said image of step d. by an amount of distance that correlates to said relative spacing;
  i. superimposing said B-scan image of step d. with said offset image of step h. to form a composite image with all of the detected features at any point in said composite image relating directly to a same point of said first surface of said workpiece.

5. The method as in claim 1 wherein said B-scan image of step d. is one of a threshold type B-scan, B'-scan and a profile generated B-scan in conjunction with an amplitude type B-scan.

6. The method as in claim 2 wherein said B-scan image of steps d. and j. are each independently selected to be one of a threshold type B-scan, a B'-scan and a profile generated B-scan in conjunction with an amplitude type B-scan, to enhance the detection of a feature of interest in said workpiece.

7. A method for producing an ultrasonic B-scan image or B'-scan image of a weld in a workpiece having a top and bottom surface to locate the basemetal to weld interface, the weld thickness and location of a weld toe, the basemetal thickness, the thickness of dissimilar materials, the location of the external surface geometry, and to do this from one or both sides of the weld; ostensibly to locate anomalies of any size and orientation, said method comprising the steps of:
  a. directing a first sonic beam perpendicular to a first surface of said workpiece and said weld, and imaging a corresponding reflected response as a threshold B-scan;
  b. directing a second sonic beam having a first frequency at an angle of substantially 45 degrees to said first surface of said workpiece toward said weld, and imaging a corresponding reflected response as an amplitude B-scan;
  c. individually developing B-scan signals from each of said detected reflections of said first and second sonic beams from steps a. and b.; and
  d. superimposing said B-scan signals of step c. to enable the determination of the existence and location of various detected features of said workpiece and said weld.

8. The method as in claim 7 wherein:
said method further includes the step of:
  e. directing a third sonic beam having a second frequency that is higher than said first frequency at an angle of substantially 45 degrees to said first surface of said workpiece toward said weld, and imaging a corresponding reflected response as one of a threshold B-scan and an amplitude B-scan to best detect a desired feature;
step c. includes the step of:
  f. individually developing a B-scan signal from said detected reflection of said third sonic beam of step e.; and step d. includes the step of:
  g. superimposing said B-scan signal of step f. together with those of steps c. to enable the determination of the existence and location of various detected features of said workpiece and said weld.

9. A multichannel ultrasonic imaging system to produce a superpositioned ultrasonic B-scan image of a workpiece having a top and bottom surface to locate flaws, failures and anomalies of various types in a variety of materials, and to map external surface geometry comprising:
first data channel electronics including:
  a first sonic beam transducer disposed to direct a first sonic beam of a first frequency toward a first surface of said workpiece at a first angle with respect to said first surface and to detect reflections of said first sonic beam from said workpiece over time; and
  a first encoder coupled to said first sonic beam transducer to preprocess said reflections of said first sonic beam from said workpiece;
second data channel electronics including:
  a second transducer disposed to exercise said first surface of said workpiece and generate data relative to said first surface of said workpiece; and
  a second encoder coupled to said second transducer to preprocess said data from said second transducer; and
a computer coupled to said first and second data channel electronics to develop a first B-scan image from said preprocessed reflections from said first encoder, to develop a second image from said preprocessed data from said second encoder, and to superposition said B-scan image from said reflections from said first encoder with said data image from said second encoder to create a composite of said images from which to determine the existence and location of various detected features of said workpiece.

10. The multichannel ultrasonic imaging system as in claim 9 wherein:
said second transducer is a second sonic beam transducer disposed to direct a second sonic beam of a second frequency toward a first surface of said workpiece at a second angle with respect to said first surface and to detect reflections of said second sonic beam from said workpiece over time;
said second encoder coupled to said first sonic beam transducer to preprocess said reflections of said second sonic beam from said workpiece; and
said computer independently develops a second B-scan image from said detected reflections of said second sonic beam, and superpositions said first and second B-scan images to create a composite B-scan image from which to determine the existence and location of various detected features of said workpiece.

11. The multichannel ultrasonic imaging system as in claim 9 wherein:
said second transducer is a stylus disposed to be in contact with said first surface of said workpiece to follow a profile of said first surface as said workpiece is scanned;
said second encoder coupled to said stylus electronically monitors positions of said stylus to develop an signal corresponding to said profile of said first surface as said workpiece is scanned; and
said computer independently develops an image of said profile of said first surface, and superpositions said first B-scan image with said image of said profile to create a composite B-scan image from which to determine the existence and location of various detected features of said workpiece.

12. The multichannel ultrasonic imaging system as in claim 9 wherein:

a relative spacing between said first sonic beam transducer and said second transducer; and said computer in superpositioning of said first B-scan image and said second image first offsets said second image an amount of distance that correlates to said relative spacing, and then superimposing said first B-scan image with said offset second image to form a composite image with all of the detected features at any point in said composite image relating directly to a same point of said first surface of said workpiece.

13. The multichannel ultrasonic imaging system as in claim 9 wherein said first B-scan image is one of a threshold type B-scan, B'-scan and a profile generated B-scan in conjunction with an amplitude type B-scan.

14. The multichannel ultrasonic imaging system as in claim 10 wherein each of said first and second B-scan images is independently selected to be one of a threshold type B-scan, B'-scan and a profile generated B-scan in conjunction with an amplitude type B-scan.

* * * * *